US010131623B2

United States Patent
Dyballa et al.

(10) Patent No.: US 10,131,623 B2
(45) Date of Patent: *Nov. 20, 2018

(54) PROCESS FOR PREPARING SYMMETRIC PINCER LIGANDS FROM THE GROUP OF THE M-TERPHENYL COMPOUNDS

(71) Applicant: EVONIK DEGUSSA GMBH, Essen (DE)

(72) Inventors: Katrin Marie Dyballa, Recklinghausen (DE); Robert Franke, Marl (DE); Dirk Fridag, Haltern am See (DE); Siegfried R. Waldvogel, Gau-Algesheim (DE); Bernd Elsler, Bonn (DE); Anton Wiebe, Neuwied (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/239,966

(22) Filed: Aug. 18, 2016

(65) Prior Publication Data

US 2017/0050918 A1 Feb. 23, 2017

(30) Foreign Application Priority Data

Aug. 21, 2015 (DE) .................. 10 2015 216 000

(51) Int. Cl.
*C07C 217/84* (2006.01)
*B01J 31/02* (2006.01)
(Continued)

(52) U.S. Cl.
CPC ......... *C07C 217/84* (2013.01); *B01J 31/0271* (2013.01); *C07C 41/30* (2013.01);
(Continued)

(58) Field of Classification Search
None
See application file for complete search history.

(56) References Cited

U.S. PATENT DOCUMENTS

| 8,747,645 B2 | 6/2014 | Stecker et al. |
| 2017/0050910 A1* | 2/2017 | Dyballa .................. C07C 43/23 |

FOREIGN PATENT DOCUMENTS

| CN | 1753967 A | 3/2006 |
| CN | 102459707 A | 5/2012 |

OTHER PUBLICATIONS

Lips et al. "Synthesis of meta-Terphenyl-2,2"-diols by Anodic CCC Cross-Coupling Reactions", Angewandte Chmie International Edition, 2016, 55, 10872-10876.*

(Continued)

*Primary Examiner* — Clinton A Brooks
(74) *Attorney, Agent, or Firm* — Smith, Gambrell & Russell, LLP (57) ABSTRACT

The present invention relates to a process for preparing compounds of the formula ABA

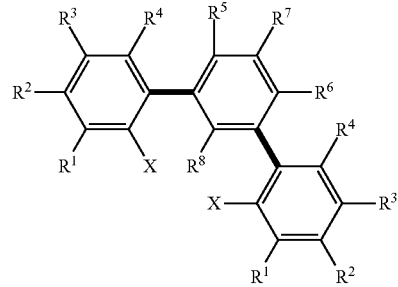

by reacting a compound of the formula (A)

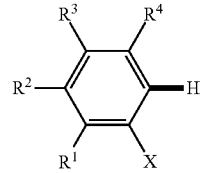

with a compound of the formula (B)

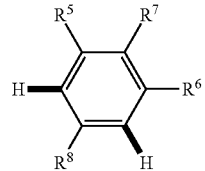

with X=—OR' or —NHR' and R'=H or a protecting group function and $R^1$, $R^2$, $R^3$, $R^4$, $R^5$, $R^6$, $R^7$ and $R^8$ are each independently selected from the group comprising hydrogen, ($C_1$-$C_{12}$)-alkyl, O—($C_1$-$C_{12}$)-alkyl, ($C_6$-$C_{20}$)-aryl, O—($C_6$-$C_{20}$)-aryl, where two of the $R^1$ to $R^4$ radicals may also be joined via a covalent bond, and halogen, which is characterized in that the reaction is conducted electrochemically.

26 Claims, 2 Drawing Sheets

(51) Int. Cl.
  C07C 43/23    (2006.01)
  C25B 3/10     (2006.01)
  C07C 41/30    (2006.01)
  C07C 213/08   (2006.01)
  C07C 269/06   (2006.01)

(52) U.S. Cl.
  CPC ............ *C07C 43/23* (2013.01); *C07C 213/08* (2013.01); *C07C 269/06* (2013.01); *C25B 3/10* (2013.01); *Y02P 20/55* (2015.11)

(56) References Cited

OTHER PUBLICATIONS

Lips et al. "Synthesis of meta-Terphenyl-2,2"-diols by Anodic CCC Cross-Coupling Reactions", Angewandte Chmie International Edition, 2016, 55, 10872-10876, cover page showing online publication date.*

European Search Report for European Application No. 16 18 2752 dated Dec. 16, 2016 (1 page).

B. G. Pring. An Investigation of the Acid-catalyzed Demethylation and Dehydration of Some Tetramethoxyterphenyls. Acta Chem. Scand. 1973, 27, 3873-3880.

R. S. Grewal, H. Hart, T. K. Vinod. Oxacyclophanes Based on a m-Terphenyl Framework. J. Org. Chem. 1992, 57, 2721-2726.

S. Sarkar, A. R. Carlson, M. K. Veige, J. M. Falkowski, K. A. Abboud, A. S. Veige. Synthesis, Characterization, and Reactivity of a $d^2$, Mo(IV) Complex Supported by a New OCO-Trianionic Pincer Ligand. J. Am. Chem. Soc. 2008, 130, 1116-1117.

C. Poriel, R. Metivier, J. Rault-Berthelot, D. Thirion, F. Barriere, O. Jeannin. A robust pure hydrocarbon derivative based on the (2,1-b)-indenofluorenyl core with high triplet energy level. Chem. Commun. 2011, 47, 11703-11705.

A. Kirste, B. Elsler, G. Schnakenburg, S. R. Waldvogel. Efficient Anodic and Direct Phenol-Arene C,C Cross-Coupling: The Benign Role of Water or Methanol, J. Am. Chem. Soc. 2012, 134, 3571-3576.

A. Kirste, S. Hayashi, G. Schnakenburg, I. M. Malkowsky, F. Stecker, A. Fischer, T. Fuchigami, S. R. Waldvogel. Highly Selective Electrosynthesis of Biphenols on Graphite Electrodes in Fluorinated Media. Chem. Eur. J. 2011, 17, 14164-14169.

B. Elsler, D. Schollmeyer, K. M. Dyballa, R. Franke, S. R. Waldvogel. Metal- and Reagent-Free Highly Selective Anodic Cross-Coupling Reaction of Phenols. Angew. Chem. Int. Ed. 2014, 53, 5210-5213.

A. Kirste, M. Nieger, I. M. Malkowsky, F. Stecker, A. Fischer, S, R. Waldvogel. ortho-Selective Phenol-Coupling Reaction by Anodic Treatment on Boron-Doped Diamond Electrode Using Fluorinated Alcohols. Chem. Eur. J. 2009, 15, 2273-2277.

Chinese Office Action dated Jun. 26, 2018 for Chinese Patent Application No. 201610688235 (6 pages in Chinese with English machine translation).

Chinese search report dated Jun. 14, 2018 for Chinese Patent Application No. 201610688235 (6 pages in Chinese with English machine translation).

Kayal, A., et al. Ortho-Linked Polyaryloxide Ligands and Their Titanium Complexes. Inorganic Chemistry. 2000. vol. 39, pp. 3696-3704 (3 pages in English).

* cited by examiner

PROCESS FOR PREPARING SYMMETRIC PINCER LIGANDS FROM THE GROUP OF THE M-TERPHENYL COMPOUNDS

The present invention relates to a process for preparing compounds of the formula ABA

(ABA)

by reacting a compound of the formula (A)

(A)

with a compound of the formula (B)

(B)

with X=—OH or —NR'R" and R'=H or a protecting group function and R"=H or a protecting group function and where R' and R" may be covalently joined to one another and $R^1$, $R^2$, $R^3$, $R^4$, $R^5$, $R^6$, $R^7$ and $R^8$ are each independently selected from the group comprising hydrogen, hydrocarbyl radicals, and hydrocarbyl radicals having heteroatoms, where adjacent radicals from the group of the $R^1$ to $R^8$ radicals may also be joined via a covalent bond, which is characterized in that the reaction is conducted electrochemically.

Adjacent radicals in the context of the present invention are those radicals bonded to directly adjacent carbon atoms. In the case of compound (A), for example, the $R^1$ and $R^2$ radicals. Examples of such radicals are, for example, —O—(CH$_2$)$_z$—O— with z=1 to 5, preferably 1 to 3, more preferably 1.

The compounds of the formula ABA are symmetric compounds from the group of the m-terphenyls (hereinafter also called, as the case may be, m-terphenyl compounds or symmetric pincer ligands, especially NCN or OCO pincer ligands).

Terphenyls refer to diphenylbenzenes. m-Terphenyls is the name usually given to 1,3-diphenylbenzenes. Compounds from the group of the m-terphenyls consequently contain a characteristic 1,3-diphenylbenzene structure. In the context of the present invention, symmetric pincer ligands are understood to mean compounds having a 1,3-diphenylbenzene unit where the two outer rings are not arenes but phenols or anilines or phenol or aniline derivatives. The OH or NR$_2$ groups of the two phenyl units are each arranged ortho to the arene component.

Symmetric pincer ligands are understood in the context of the present invention to mean compounds in which the two phenols or anilines are identical. In the context of the application, the arene component between the two different phenyl components need not necessarily be symmetric; in other words, when a mirror plane is placed on the arene molecule, one side need not necessarily be an image of the other side. Even when the arene component is intrinsically unsymmetric, the product, i.e. the resulting pincer ligand, in the context of the application, should be regarded as symmetric.

In addition, in the context of the present invention, the following numbering of the positions in the arene component (B) is used:

(B)

$R^5$ is defined as the substituent on carbon atom 1 in the benzene ring, $R^6$ as the substituent on carbon atom 2, $R^7$ as the substituent on carbon atom 3, $R^8$ as the substituent on carbon atom 5.

The conventional synthesis of OCO pincer ligands has to date been restricted to symmetric derivatives. The known processes enable $C_{Ar}$-$C_{Ar}$ bond formation, for example, via Ullmann coupling (B. G. Pring, Acta Chem. Scand. 1973, 27, 3873-3880), Grignard-Wurtz coupling (R. S. Grewal, H. Hart, T. K. Vinod, J. Org. Chem. 1992, 57, 2721-2726.), or palladium-catalysed coupling reactions (S. Sarkar, A. R. Carlson, M. K. Veige, J. M. Falkowski, K. A. Abboud, A. S. Veige, J. Am. Chem. Soc. 2008, 130, 1116-1117). Before the actual coupling reactions, protection of the hydroxyl function is necessary, which in most cases is achieved by means of methylation. In all known cases, it is necessary to conduct the reaction with exclusion of moisture and under anaerobic conditions.

Scheme 1: State of the art for preparation of symmetric OCO pincer ligands (S. Sarkar, A. R. Carlson, M. K. Veige, J. M. Falkowski, K. A. Abboud, A. S. Veige, J. Am. Chem. Soc. 2008, 130, 1116-1117).

a)

Scheme 2: State of the art for preparation of symmetric NCN pincer ligands (C. Poriel, R. Metivier, J. Rault-Berthelot, D.Thirion, F. Barriere, O. Jeannin, Chem. Commun. 2011, 47, 11703-11705).

A great disadvantage of the known methods for cross-coupling of aniline derivatives or phenol derivatives with arenes is the need for dry solvents and exclusion of air during the coupling reaction. In conventional cross-coupling methods, the protection of the amine or hydroxyl functionality is necessary in most cases. In addition, for a regioselective cross-coupling, leaving functionalities which are introduced in the substrates used occur as environmentally problematic reaction wastes after the actual coupling reaction (see Scheme 1). Tolerance for functional groups is often restricted by the reagents used, and so usable derivatives are particularly those having a low degree of substitution. Toxic by-products (for example bromine compounds) often occur during the reaction, and have to be removed from the desired product in a complex manner and disposed of at great cost. Moreover, the product has to be prepared over very many stages, which is likewise very disadvantageous (see Schemes 1 and 2). Increasingly scarce raw materials are making the preparation of ligand systems by palladium-catalysed cross-couplings or chemical oxidizing agents very costly.

The preparation of symmetric pincer ligands by a conventional route is very complex. Many different reagents and solvents are required and a very large amount of waste is additionally produced, which should be avoided from an environmental and economic point of view.

The problem addressed by the present invention was therefore that of providing a simple process for preparing symmetric pincer ligands from the group of the m-terphenyl compounds which avoids one or more disadvantages of the prior art.

It has been found that, surprisingly, this problem can be solved by conducting the coupling reaction electrochemically.

The present invention therefore provides a process as claimed in the claims.

The present invention likewise provides compounds of the formula CDC as defined below.

The present invention also provides for the use of the compounds of the invention as ligand for preparation of metal-ligand catalyst systems.

The process of the invention has the advantage that the electrochemical conversion significantly simplifies the preparation of symmetric m-terphenyl compounds, since exclusion of moisture or compliance with anaerobic reaction conditions cannot be assured. Moreover, the synthesis proceeds directly via one stage and it is possible to dispense with a multitude of synthesis steps. This leads, inter alia, to a lower degree of complexity in the performance of the process and to an overall process which is much simpler and hence more economically viable.

The electrochemical reaction also has the advantage that the formation of unwanted by-products can be distinctly reduced.

The electrochemical cross-coupling dispenses with the use of costly and toxic catalysts and the introduction of activating leaving functionalities, for example boron or bromine compounds, prior to the coupling reaction.

According to the way in which the process of the invention is executed, the process for the first time allows the direct synthesis of symmetric compounds with a low level of synthetic complexity and simultaneously high tolerance for functional groups in the substrates used.

Furthermore, in the process of the invention, it is possible to partly or preferably completely dispense with the use of chemical oxidizing agents. In this way, the risk of formation of by-products or contamination of the compounds by residues of the oxidizing agents is avoided.

The process of the invention also has the advantage that a great variety of different m-terphenyl compounds can be prepared, which were obtainable only at great cost and inconvenience, if at all, by the processes known from the prior art.

More particularly, the process of the invention has the advantage that the m-terphenyl compounds (m-terphenyls) of the invention can be prepared therewith.

The process according to the invention, the compounds according to the invention and the use thereof are described hereinafter by way of example, without any intention that the invention be restricted to these illustrative embodiments. When ranges, general formulae or compound classes are specified hereinbelow, these shall encompass not just the corresponding ranges or groups of compounds that are explicitly mentioned but also all subranges and subgroups of compounds obtainable by extracting individual values (ranges) or compounds. Where documents are cited in the context of the present description, their content shall fully form part of the disclosure content of the present invention, particularly in respect of the substantive matter in the context for which the document was cited. Where per cent figures are given hereinafter, these are figures in % by volume unless stated otherwise. Where mean values are reported hereinafter, these are the numerical mean, unless stated otherwise. Where properties of a material are referred to hereinafter, for example viscosities or the like, these are properties of the material at 25° C., unless stated otherwise.

The process according to the invention for preparing compounds of the formula ABA

(ABA)

by reacting a compound of the formula (A)

(A)

with a compound of the formula (B)

(B)

with X=—OH or —NR'R";

and R'=H or a protecting group function, preferably selected from the group comprising tert-butyloxycarbonyl, methyloxycarbonyl, benzyloxycarbonyl, phenyloxycarbonyl, acetyl, trifluoroacetyl, benzoyl, sulphonyl and sulphenyl;

and R"=H or a protecting group function, preferably selected from the group comprising tert-butyloxycarbonyl, methyloxycarbonyl, benzyloxycarbonyl, phenyloxycarbonyl, acetyl, trifluoroacetyl, benzoyl, sulphonyl and sulphenyl;

or R' and R" may together form covalently bonded protecting group radicals, preferably radicals of the formula PGa or PGb PGa PGb and $R^1$, $R^2$, $R^3$, $R^4$, $R^6$ and $R^8$ are each independently selected from the group comprising hydrogen, $(C_1-C_{12})$- alkyl, —O—(C$_1$-C$_{12}$)-alkyl, —N[(C$_1$-C$_{12}$)-alkyl]$_2$, —NH (C$_1$-C$_{12}$)-alkyl, (C$_6$-C$_{20}$)-aryl, O—(C$_6$-C$_{20}$)-aryl and halogen, preferably consisting of hydrogen, (C$_1$-C$_{12}$)-alkyl, —O—(C$_1$-C$_{12}$)-alkyl, —N[(C$_1$-C$_{12}$)-alkyl]$_2$ and halogen, more preferably consisting of hydrogen, (C$_1$-C$_{12}$)-alkyl and —O—(C$_1$-C$_{12}$)-alkyl;

and R$^5$ and R$^7$ are each independently selected from the group comprising (C$_1$-C$_{12}$)-alkyl, —O—(C$_1$-C$_{12}$)-alkyl, —N[(C$_1$-C$_{12}$)-alkyl]$_2$, —NH(C$_1$-C$_{12}$)-alkyl, (C$_6$-C$_{20}$)-aryl, —O—(C$_6$-C$_{20}$)-aryl, halogen, preferably consisting of (C$_1$-C$_{12}$)-alkyl, —O—(C$_1$-C$_{12}$)-alkyl, —N[(C$_1$-C$_{12}$)-alkyl]$_2$ and halogen, and more preferably consisting of (C$_1$-C$_{12}$)-alkyl, —O—(C$_1$-C$_{12}$)-alkyl and —N[(C$_1$-C$_{12}$)-alkyl]$_2$;

where adjacent radicals from the group of the R$^1$ to R$^8$ radicals may be joined via a covalent bond, characterized in that the reaction is conducted electrochemically.

In the context of the present invention, halogen is understood to mean fluorine, chlorine, bromine or iodine, especially fluorine, chlorine and bromine. The term "alkyl" in the context of the present invention is understood to mean a linear or branched hydrocarbon radical in which one or more hydrogen atoms may optionally be replaced, preferably by halogen atoms or hydroxyl or alk(yl)oxy groups. Aryl in the context of the present invention means aromatic hydrocarbyl radicals, for example phenyl-(C$_6$H$_5$—), naphthyl-(C$_{10}$H$_7$—), anthryl-(C$_{14}$H$_9$—), preferably phenyl, in which one or more hydrogen atoms may optionally be replaced, preferably by alkyl or alk(yl)oxy groups.

In the context of the invention, the expression "—(C$_1$-C$_{12}$)-alkyl" encompasses straight-chain and branched alkyl groups. Preferably, these groups are unsubstituted straight-chain or branched —(C$_1$-C$_8$)-alkyl groups and most preferably —(C$_1$-C$_6$)-alkyl groups. Examples of —(C$_1$-C$_{12}$)-alkyl groups are especially methyl, ethyl, propyl, isopropyl, n-butyl, isobutyl, sec-butyl, tert-butyl, n-pentyl, 2-pentyl, 2-methylbutyl-, 3-methylbutyl-, 1,2-dimethylpropyl-, 1,1-dimethylpropyl, 2,2-dimethylpropyl-, 1-ethylpropyl-, n-hexyl-, 2-hexyl-, 2-methylpentyl-, 3-methylpentyl-, 4-methylpentyl-, 1,1-dimethylbutyl-, 1,2-dimethylbutyl-, 2,2-dimethylbutyl-, 1,3-dimethylbutyl-, 2,3-dimethylbutyl-, 3,3-dimethylbutyl-, 1,1,2-trimethylpropyl-, 1,2,2-trimethylpropyl-, 1-ethylbutyl-, 1-ethyl-2-methylpropyl-, n-heptyl-, 2-heptyl-, 3-heptyl-, 2-ethylpentyl-, 1-propylbutyl-, n-octyl-, 2-ethylhexyl-, 2-propylheptyl-, nonyl-, decyl- and dodecyl-. The "(C$_1$-C$_{12}$)-alkyl and O—(C$_1$-C$_{12}$)-alkyl" radicals may each be unsubstituted or substituted by one or more identical or different radicals selected from (C$_3$-C$_{12}$)-cycloalkyl, (C$_3$-C$_{12}$)-heterocycloalkyl, (C$_6$-C$_{20}$)-aryl, fluorine, chlorine, cyano, formyl, acyl and alkoxycarbonyl.

The elucidations relating to the expression "—(C$_1$-C$_{12}$)-alkyl" also apply to the alkyl groups in —O—(C$_1$-C$_{12}$)-alkyl, i.e. in —(C$_1$-C$_{12}$)-alkoxy. Preferably, these groups are unsubstituted straight-chain or branched —(C$_1$-C$_6$)-alkoxy groups.

In the context of the present invention, the expression "—(C$_6$-C$_{20}$)-aryl" encompasses mono- or polycyclic aromatic hydrocarbyl radicals. These have 6 to 20 ring atoms, more preferably 6 to 14 ring atoms, especially 6 to 10 ring atoms. Aryl is preferably —(C$_6$-C$_{10}$)-aryl and —(C$_6$-C$_{10}$)-aryl-(C$_6$-C$_{10}$)-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

Substituted —(C$_6$-C$_{20}$)-aryl groups may have one or more (e.g. 1, 2, 3, 4 or 5) substituents, depending on the ring size. These substituents are preferably each independently selected from —H, —(C$_1$-C$_{12}$)-alkyl, —O—(C$_1$-C$_{12}$)-alkyl, —O—(C$_6$-C$_{20}$)-aryl, —(C$_6$-C$_{20}$)-aryl, -halogen (such as Cl, F, Br, I), —COO—(C$_1$-C$_{12}$)-alkyl, —CONH—(C$_1$-C$_{12}$)-alkyl, —(C$_6$-C$_{20}$)-aryl-CON[(C$_1$-C$_{12}$)-alkyl]$_2$, —CO—(C$_1$-C$_{12}$)-alkyl, —CO—(C$_6$-C$_{20}$)-aryl, —COOH, —OH, —SO$_3$H, —SO$_3$Na, —NO$_2$, —CN, —NH$_2$, —N[(C$_1$-C$_{12}$)-alkyl]

The electrochemical conversion is preferably effected in such a way that aa) a mixture of at least one solvent and at least one conductive salt is produced, bb) the compounds to be converted are added to this mixture, with addition of the compound of the formula (A) preferably in a molar excess based on the compound (B), cc) at least two electrodes are introduced into the reaction solution obtained in bb) and a voltage is applied to the electrodes, dd) the compounds (A) and (B) are converted to the compound (ABA), ee) the voltage is switched off, and optionally ff) the compound (ABA) is isolated and/or purified.

In the process according to the invention, the compounds (A) and (B) are preferably used in such amounts that the molar ratio of the compound (A) to the compound (B) is in the range from 1.5:1 to 4:1, preferably from 1.8:1 to 2.5:1 and more preferably 2:1.

In a preferred embodiment of the process according to the invention, the compounds of the formula (A) used are those compounds in which X=—NR'R" with R' and R" each independently selected from the group comprising hydrogen, tert-butyloxycarbonyl, methyloxycarbonyl, benzyloxycarbonyl, phenyloxycarbonyl, acetyl, trifluoroacetyl, benzoyl, sulphonyl and sulphenyl, preferably consisting of hydrogen, tert-butyloxycarbonyl, methyloxycarbonyl, benzyloxycarbonyl, phenyloxycarbonyl, acetyl, trifluoroacetyl and benzoyl, and more preferably consisting of hydrogen, acetyl and trifluoroacetyl; or R' and R" are joined covalently to one another, preferably via one of the following groups PGa or PGb:

PGa

PGb

Preferably, one of the R' and R" radicals =H. More preferably, X=—NH$_2$.

If, in the process according to the invention, compounds of the formula (A) used are those in which R' or R" is not H, such compounds can be obtained in a known manner from the compounds of the formula (A) with R' and/or R"=H by introducing a protecting group. Protecting groups and the introduction thereof are known to those skilled in the art and can be found in the standard technical literature (in this regard, see also: P. G. M. Wuts, T. W. Greene "Greene's Protective Groups in Organic Synthesis", fourth edition, 2007, John Wiley and Sons; Hoboken, N.J.).

In a further preferred embodiment of the process according to the invention, the compound of the formula (A) used is preferably a compound (A) in which X=—NH$_2$.

In a further preferred embodiment of the process according to the invention, the compound of the formula (A) used is preferably a compound (A) in which X=—OH.

In the process according to the invention, preference is given to using those compounds of the formula (B) in which $R^6$ and $R^8$ are identical and are preferably hydrogen.

In the process according to the invention, preference is given to using those compounds of the formula (B) in which $R^5$ and $R^7$ are different and are preferably ($C_1$-$C_{12}$)-alkyl, O—($C_1$-$C_{12}$)-alkyl or —N[($C_1$-$C_{12}$)-alkyl]$_2$.

Preference is given to using, in the process according to the invention, those compounds of the formula (B) in which $R^6$ and $R^8$ are identical and are preferably hydrogen and in which $R^5$ and $R^7$ are different and are preferably ($C_1$-$C_{12}$)-alkyl, O—($C_1$-$C_{12}$)-alkyl or —N[($C_1$-$C_{12}$)-alkyl]$_2$.

The electrochemical reaction conducted in accordance with the invention can be conducted, for example, in accordance with the processes for electrochemical coupling of carbon-carbon bonds described by a.) A. Kirste, B. Elsler, G. Schnakenburg, S. R. Waldvogel, J. Am. Chem. Soc. 2012, 134, 3571-3576, b.) A. Kirste, S. Hayashi, G. Schnakenburg, I. M. Malkowsky, F. Stecker, A. Fischer, T. Fuchigami, S. R. Waldvogel, Chem. Eur. J. 2011, 17, 14164-14169, c.) B. Elsler, D. Schollmeyer, K. M. Dyballa, R. Franke, S. R. Waldvogel, Angew. Chem. Int. Ed. 2014, 53, 5210-5213, and d.) A. Kirste, M. Nieger, I. M. Malkowsky, F. Stecker, A. Fischer, S. R. Waldvogel, Chem. Eur. J. 2009, 15, 2273-2277.

The electrochemical reaction can be conducted in all suitable electrolysis cells known from the prior art. Preference is given to using, in the process according to the invention, a flange cell, a beaker cell or a screening cell. Such cells are described in the literature, and the first two glass cells can be sourced, for example, under this name at HWS Labortechnik Mainz.

The cell has at least two electrodes. The electrodes used may be standard commercial electrodes. The anodes used may preferably, for example, be BDD (0.015 mm of boron-doped diamond on silicon or 0.05 mm of boron-doped diamond on niobium), or platinum, isostatic graphite or glassy carbon electrodes. The cathodes used are preferably BDD, nickel mesh or glassy carbon electrodes. Such BDD electrodes (boron-doped diamond on a support, for example niobium or silicon) are available, for example, under the DIACHEM name from Condias GmbH Itzehoe. The rest of the electrodes are available from standard chemical and material suppliers, for example Goodfellow or Aldrich.

The electrochemical reaction is preferably conducted in the presence of a solvent. The solvent used is preferably a solvent from the group of acetonitrile, propylene carbonate, methyl carbonate, nitromethane, ethylene glycol dimethyl ether, methanesulphonic acid, benzene, toluene, water, methanol, ethanol, propanol, isopropanol, halogenated solvents or halogenated or non-halogenated acids or mixtures thereof.

Solvents used are preferably a carboxylic acid, preferably formic acid, a fluorinated carboxylic acid or a fluorinated alcohol, preferably trifluoroacetic acid or 1,1,1,3,3,3-hexafluoro-2-propanol (HFIP), preferably 1,1,1,3,3,3-hexafluoro-2-propanol.

Particular preference is given to using, as solvents, methanol, formic acid, trifluoroacetic acid, hexafluoroisopropanol or mixtures thereof, preferably methanol, hexafluoroisopropanol or mixtures thereof, and more preferably hexafluoroisopropanol (1,1,1,3,3,3-hexafluoro-2-propanol).

The electrochemical reaction is preferably conducted in the presence of at least one conductive salt, the conductive salts used preferably being those selected from the group of tetra($C_1$-$C_6$-alkyl)ammonium and 1,3-di($C_1$-$C_6$-alkyl)imidazolium salts, with the proviso that the alkyl groups may be halogen-substituted, especially fluorine-substituted. Preference is given to using those conductive salts having counterions selected from the group comprising arsenate, sulphate, hydrogensulphate, alkylsulphate, alkylphosphate, perchlorate, fluoride, arylsulphate, hexafluorophosphate and tetrafluoroborate. Preferred conductive salts are those from the group of quaternary ammonium borates, ammonium fluoroalkylphosphates, ammonium fluoroalkylarsenates, ammonium trifluoromethylsulphonates, ammonium bis(fluoromethanesulphon)imides, ammonium tris(fluoromethanesulphonyl)methides, methyltributylammonium methylsulphate, methyltriethylammonium methylsulphate, tetrabutylammonium hexafluorophosphate, tetraethylammonium tetrafluoroborate, lithium hexafluorophosphate or tetraethylammonium tetrafluoroborate. Particular preference is given to using methyltriethylammonium methylsulphate or Bu$_3$NMe$^+$MeOSO$_3^-$ (methyltributylammonium methylsulphate), very particular preference to methyltributylammonium methylsulphate, as conductive salt.

The conductive salt is preferably used in a concentration of 0.001 to 10 mol/l, preferably 0.01 to 1 mol/l, more preferably of 0.075 to 0.125 mol/l and most preferably of 0.09 mol/l, based on the reaction mixture.

Preference is given to using, in the process according to the invention, at least a sufficient amount of compound A in each case that the concentration is from 0.001 to 5 mol/l, preferably from 0.05 to 0.5 mol/l, more preferably from 0.1 to 0.3 mmol/l and especially preferably 0.15 mol/l of reaction mixture.

The electrochemical reaction is preferably conducted at room temperature or elevated temperature. Preferably, the electrochemical reaction is conducted at a temperature in the electrolysis cell in the range from 25 to 80° C., preferably from 35 to 70° C. and preferably from 45 to 55° C.

The electrochemical reaction is preferably conducted in a galvanostatic manner.

In the performance of the electrochemical reaction, the current is preferably chosen such that the current density is from 1 to 10 mA/cm$^2$, preferably from 2 to 5.5 mA/cm$^2$, preferably from 2.5 to 3 mA/cm$^2$ and more preferably 2.8 mA/cm$^2$. To conduct the electrochemical reaction, preference is given to applying a (terminal) voltage between the electrodes in the range from 2 to 10 V, preferably 2.5 to 7.5 V and preferably from 3 to 6 V.

Two reaction schemes below show, by way of example, the performance of the process according to the invention. The $R^1$ to $R^8$ radicals used in the schemes are as defined above. The coupling of a substituted phenol to a 1,3-disubstituted arene which may likewise be substituted in 2 and 5 positions leads to a compound of the formula ABA.

Scheme 3: General reaction.

Scheme 4: Preparation of 2,2″-dihydroxy-3,3″,4′-trimethoxy-5,5″,2′-trimethyl[1,1′;5′1″]terphenyl(2) as compound of the formula (ABA)

Such compounds have not been described to date by a conventional route or are obtainable only with a high level of synthetic complexity.

The process of the invention is preferably conducted in such a way that the reaction in the electrochemical process steps, preferably the entire reaction, is conducted without the use of organic oxidizing agents.

With the process of the invention, it is especially possible to prepare the inventive compounds of the formula (CDC).

The inventive compounds of the formula (CDC)

X=—OH or —NR'R";

with R' or R" each independently selected from the group comprising hydrogen, tert-butyloxycarbonyl, methyloxycarbonyl, benzyloxycarbonyl, phenyloxycarbonyl, acetyl, trifluoroacetyl, benzoyl, sulphonyl and sulphenyl, preferably consisting of hydrogen, tert-butyloxycarbonyl, methyloxycarbonyl, benzyloxycarbonyl, phenyloxycarbonyl, acetyl, trifluoroacetyl and benzoyl, preferably consisting of hydrogen, acetyl and trifluoroacetyl; and, more preferably, R' and R" are hydrogen, or R' and R" are joined covalently to one another, preferably via one of the following groups PGa or PGb:

and $R^9$, $R^{10}$, $R^{11}$ and $R^{12}$ are each independently selected from the group comprising hydrogen, $(C_1$-$C_{12})$-alkyl, O—$(C_1$-$C_{12})$-alkyl, —N[$(C_1$-$C_{12})$-alkyl]$_2$, —NH$(C_1$-$C_{12})$-alkyl, $(C_6$-$C_{20})$-aryl, —O—$(C_6$-$C_{20})$-aryl and halogen, preferably consisting of hydrogen, $(C_1$-$C_{12})$-alkyl, O—$(C_1$-$C_{12})$-alkyl, —N[$(C_1$-$C_{12})$-alkyl]$_2$ and halogen, more preferably consisting of hydrogen, $(C_1$-$C_{12})$-alkyl, —O—$(C_1$-$C_{12})$-alkyl and —N[$(C_1$-$C_{12})$-alkyl]$_2$;

and $R^{13}$ and $R^{15}$ are each independently selected from the group comprising $(C_1$-$C_{12})$-alkyl, O—$(C_1$-$C_{12})$-alkyl, —N[$(C_1$-$C_{12})$-alkyl]$_2$;

and $R^{14}$ and $R^{16}$ are hydrogen, where adjacent radicals from the group of the $R^9$ to $R^{12}$ radicals may be joined via a covalent bond.

Preferably, in the inventive compounds of the formula (CDC), X=—OH or —NH$_2$, preferably —OH.

Preferred inventive compounds of the formula (CDC) are those which satisfy the formulae (1) and (2)

The compounds of the invention can be used as ligand for preparation of metal-ligand catalyst systems.

The present invention is described by way of example with reference to FIGS. 1 to 4, without any intention that the invention, the scope of application of which is apparent from the overall description and the claims, be restricted to the embodiments depicted in the figures. FIGS. 1 to 4 depict schematic drawings of cells as usable in the process according to the invention, and as used particularly in the examples which follow.

Figure 1:
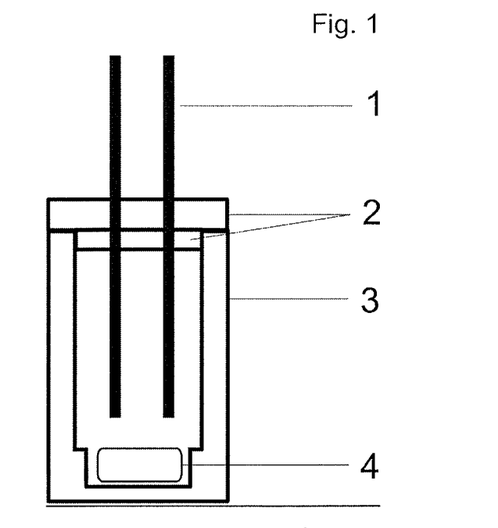
FIG. 1 shows a schematic of a screening cell. Indicated in FIG. 1 are the BDD electrodes (1), a Teflon lid (2), a Teflon beaker (3) and a stirrer magnet (4).
Figure 2:
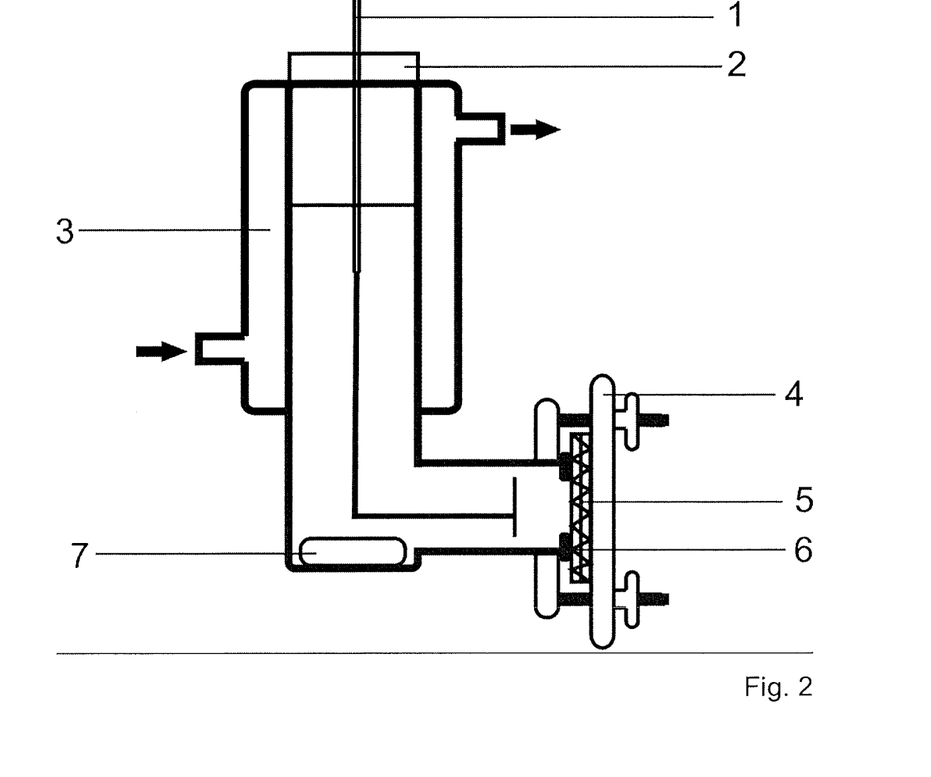

FIG. 2 shows a schematic of a flange cell (glass). Indicated in FIG. 2 are a stainless steel rod with a secured nickel mesh cathode (1), a Teflon stopper (2), a cooling jacket (glass) (3), a screw clamp (4), a BDD electrode (5), an EPDM seal (6) and a stirrer magnet (7).

Figure 3:
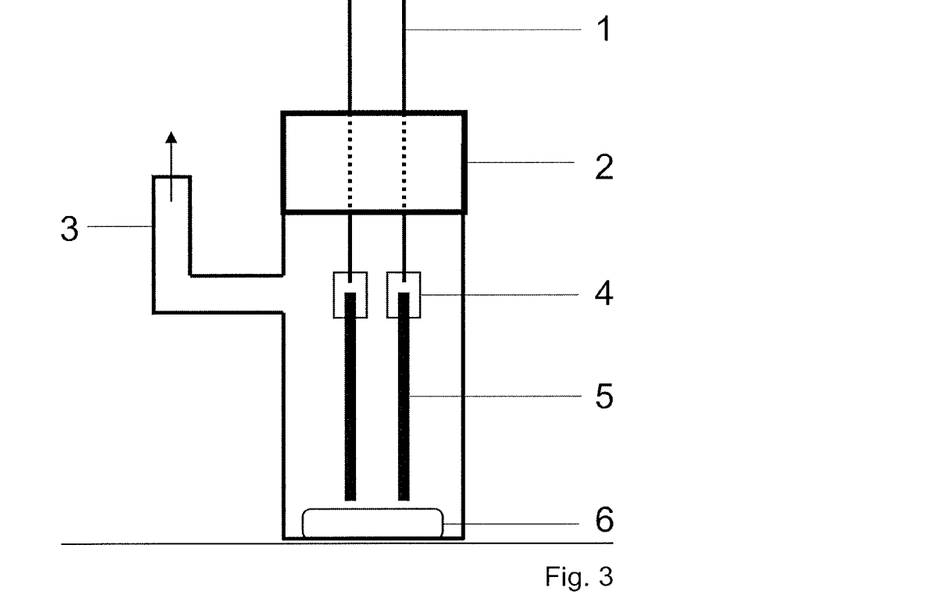

FIG. 3 shows a schematic of a small beaker cell (glass). Indicated in FIG. 3 are a stainless steel rod for forming contacts (1), a Teflon stopper (2), a cell outlet/connection (3), for example for a Dimroth condenser, electrode holders (stainless steel) (4), glassy carbon electrodes (5) and a stirrer magnet (6).

Figure 4:
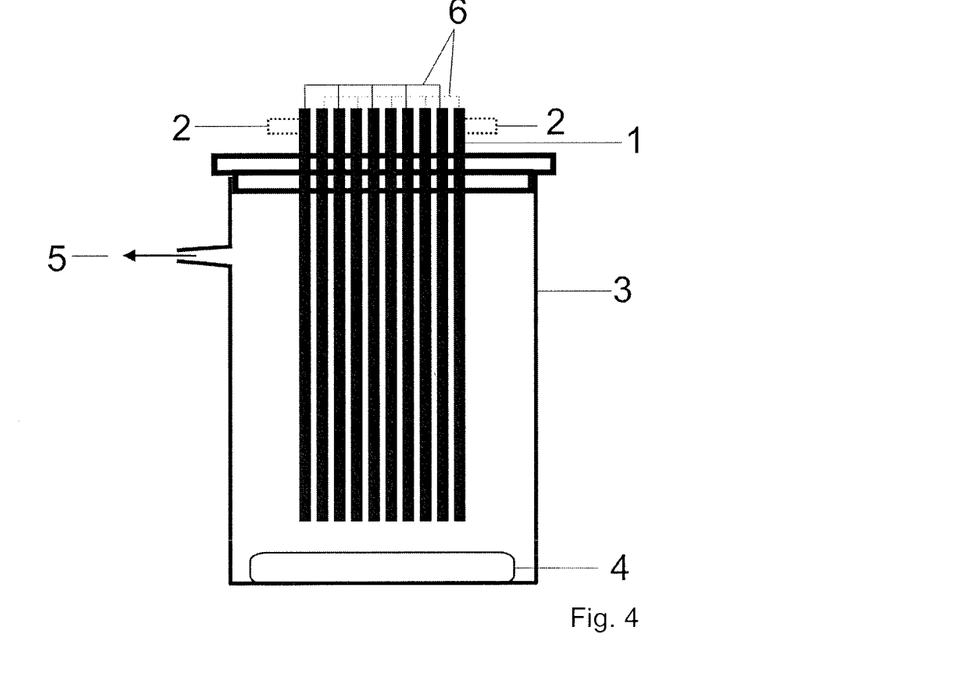

FIG. 4 shows a schematic of a large beaker cell (glass). Indicated in FIG. 4 are the BDD electrodes (1), the connections for forming contacts (2), the glass shell (3), a stirrer magnet (4), a cell outlet/connection (5), for example for a Dimroth condenser, and an electrically conductive contact (stainless steel foil) (6).

The examples adduced below illustrate the present invention by way of example, without any intention that the invention, the scope of application of which is apparent from the entirety of the description and the claims, be restricted to the embodiments specified in the examples.

EXPERIMENTAL

General Methods
Chromatography (GC/GCMS)

Preparative liquid chromatography for separation of substance mixtures was conducted using 60 M silica gel (0.040-0.063 mm) from MACHERY-NAGEL GMBH & CO. KG, Düren at a maximum pressure of 2 bar. All the eluents used (ethyl acetate, technical grade quality; cyclohexane, technical grade quality) were purified beforehand by distillation on a rotary evaporator.

Thin-layer chromatography (TLC) was conducted on ready-made PSC silica gel 60 $F_{254}$ plates from MERCK KGaA, Darmstadt. The various substances were detected first under UV light and then by staining by means of cerium-molybdophosphoric acid reagent (5.6 g of molybdophosphoric acid, 2.2 g of cerium(IV) sulphate tetrahydrate and 13.3 g of conc. sulphuric acid in 200 ml of water), followed by heating with a hot air gun.

Gas Chromatography (GC/GCMS)

The gas chromatography studies (GC) on product mixtures and pure substances were effected with the aid of the GC-2010 gas chromatograph from Shimadzu, Japan. Analysis is effected on an HP-5 quartz capillary column from Agilent Technologies, USA (length: 30 m; internal diameter: 0.25 mm; film thickness of the covalently bound stationary phase: 0.25 µm; carrier gas: hydrogen; injector temperature: 250° C.; detector temperature: 310° C.; programme: "hard" method: start temperature 50° C. for 1 min, heating rate: 15° C./min, end temperature 290° C. for 8 min). Gas chromatography-mass spectrometry analyses (GC-MS) of product mixtures and pure substances were recorded with the aid of the GC-2010 gas chromatograph combined with the GCMS-QP2010 mass detector from Shimadzu, Japan. Analysis is effected on an HP-1 quartz capillary column from Agilent Technologies, USA (length: 30 m; internal diameter: 0.25 mm; film thickness of the covalently bound stationary phase: 0.25 µm; carrier gas: hydrogen; injector temperature: 250° C.; detector temperature: 310° C.; programme: "hard" method: start temperature 50° C. for 1 min, heating rate: 15° C./min, end temperature 290° C. for 8 min; GC-MS: ion source temperature: 200° C.).

Mass Spectrometry

All electrospray ionization analyses (ESI+) were conducted on a QTof Ultima 3 from Waters Micromasses, Milford, Mass. EI mass spectra and the high-resolution EI spectra were analysed on an instrument of the MAT 95 XL sector field instrument type from Thermo Finnigan, Bremen.

NMR Spectroscopy

The NMR spectroscopy studies were conducted on multinucleus resonance spectrometers of the AC 300 or AV II 400 type from Bruker, Analytische Messtechnik, Karlsruhe. The solvent used was CDCl3. The $^1H$ and $^{13}C$ spectra were calibrated according to the residual content of undeuterated solvent using the NMR Solvent Data Chart from Cambridge Isotopes Laboratories, USA. Some of the $^1H$ and $^{13}C$ signals were assigned with the aid of H,H-COSY, H,H-NOESY, H,C-HSQC and H,C-HMBC spectra. The chemical shifts are reported as δ values in ppm. For the multiplicities of the NMR signals, the following abbreviations were used: s (singlet), bs (broad singlet), d (doublet), t (triplet), q (quartet), m (multiplet), dd (doublet of doublets), dt (doublet of triplets), tq (triplet of quartets). All coupling constants J were reported in hertz (Hz) together with the number of bonds covered. The numbering given in the assignment of signals corresponds to the numbering shown in the formula schemes, which need not necessarily correspond to IUPAC nomenclature.

Single Crystal Structure Analyses

The single crystal structure analyses were conducted in the Institute of Organic Chemistry at the Johannes Gutenberg University of Mainz on an IPDS 2T instrument from STOE & Cie GmbH, Darmstadt.

Melting Points

The relevant melting points were measured with the aid of the SG 2000 melting point determination instrument from HW5, Mainz, and were adopted in uncorrected form.

General Procedures

GP1: Electrochemical Cross-Coupling in L Cells 5 mmol of the species A to be oxidized (deficiency component) were reacted with a 2-3-fold excess (10-15 mmol) of the coupling partner B in 33 ml of 1,1,1,3,3,3-hexafluoroisopropanol (HFIP) or 33 ml of (HFIP with 18% by volume of methanol (MeOH) based on the sum total of HFIP and MeOH) in an undivided flange cell with a BDD anode and nickel mesh cathode. The conductive salt used was $Bu_3NMe^+MeOSO_3^-$ (MTBS) with a concentration of 0.09 M. The electrolysis was galvanostatic. The outer shell of the electrolysis cell was kept at a controlled temperature of about 10° C. by means of a thermostat, while the reaction mixture was stirred and heated to 50° C. with the aid of an oil bath. After the electrolysis had ended, the cell contents were transferred to a 50 ml round-bottom flask and the solvent was removed under reduced pressure on a rotary evaporator at 50° C., 200-70 mbar. Mineralization products and the conductive salt present were separated by elution by means of ethyl acetate (300 ml) using 50 g of silica gel 60. Unconverted reactant was recovered by means of short-path distillation in a Kugelrohr still (100° C., $10^{-3}$ mbar). The reaction products formed were separated by column chromatography as specified in each case.

Electrode Material:

| Anode: | BDD (15 μm diamond layer) on silicon support |
| Cathode: | nickel mesh |

Electrolysis Conditions:

| Temperature: | 50° C. |
| Current density: | 2.8 mA/cm$^2$ |
| Charge: | 2-4 F based on the deficiency component |
| Terminal voltage: | 3-6 V |

One-stage Pincer Ligand Synthesis

Example 1

2,2"-Dihydroxy-5,5"-dimethyl-2'-N,N-dimethyl-amino-3,3",4'-trimethoxy[1,1';5'1"]terphenyl (1)

The performance of the electrolysis was effected according to GP1 with 1.38 g (10 mmol, 2.0 equiv.) of 4-methylguaiacol and 0.76 g (5 mmol, 1.0 equiv.) of 3-(N,N-dimethylamino)anisole. The current was 15 mA; the amount of charge, with 4F per 3-(N,N-dimethylamino)anisole, was 1929.7 C. The crude product was prepurified by column chromatography on silica gel 60 with eluent mixture gradient of 95:5 then 9:1 and finally 4:1 (cyclohexane (CH):ethyl acetate (EA)). The fractions obtained were examined for the presence of the product and purified again on silica gel 60 with a 1:1:0.01 then 1:1:0.02 eluent (dichloromethane (DCM):cyclohexane (CH):methanol (MeOH)). A further purification of mixed fractions was conducted by Kugelrohr distillation (150° C., 180° C., 190° C. and 205° C., $10^{-3}$ mbar). The product was obtained as a yellow oil.

(1)

Yield: 54 mg (0.13 mmol, 3%)

GC (hard method, HP-5): $t_R$=18.40 min $R_f$(DCM:MeOH=99:1)=0.36

$^1$H NMR (300 MHz, CDCl$_3$) δ [ppm]=2.28 (s, 3H, H-8 o. H-11), 2.29 (s, 3H, H-8 o. H-11), 2.85 (bs, 6H, H-9), 3.77 (s, 3H, H-10), 3.81 (s, 3H, H-7 o. H-12), 3.82 (s, 3H, H-7 o. H-12), 6.40 (bs, 1H, H-13 o. H-14), 6.57 (s, 2H, H-4, H-4"), 6.59-6.61 (m, 1H, H-6'), 6.67 (m, 1H, H-3'), 6.68-6.72 (m, 2H, H-6, H-6").

$^{13}$C NMR (101 MHz, CDCl$_3$) δ [ppm]=21.10 (C-8 o. C-11), 21.22 (C-8 o. C-11), 43.44 (C-9), 55.71 (C-10), 55.81 (C-7 o. C-12), 56.91 (C-7 o. C-12), 104.68 (C-3'), 111.99, 112.07, 113.08, 113.26, 113.86, 116.59, 118.44, 120.83, 121.01, 121.50, 130.30, 132.23, 144.14, 146.66, 149.30 (C-3 o. C-3"), 150.03 (C-3 o. C-3"), 157.70 (C-4').

HRMS (ESI, pos. mode): m/z for $C_{25}H_{30}NO_5$ [M+H$^+$]: calculated: 424.2124; found: 424.2131

Elemental analysis: calculated: C: 70.90% H: 6.90% N: 3.31% found: C: 69.33% H: 6.95% N: 3.17%

Example 2

2,2"-Dihydroxy-3,3",4'-trimethoxy-5,5",2'-trimethyl[1,1';5'1"]terphenyl (2)

The electrolysis was conducted according to GP1 with 1.45 g (10.5 mmol, 2.0 equiv.) of 4-methylguaiacol and 639 mg (5.23 mmol, 1.0 equiv.) of 3-methylanisole. The current density was 2.8 mA/cm$^2$, the charge 2 F per 4-methylguaiacol (Q=2018 C). After removal of the solvent, the product mixture was purified by column chromatography on silica gel 60 with an eluent of 9:1 (CH:EA). The product was obtained as a yellowish oily substance.

(2)

Yield: 68 mg (0.17 mmol, 3%)

GC (hard method, HP-5): $t_R$=21.35 min $R_f$(Cy:EA=4:1)=0.39

$^1$H NMR (400 MHz, CDCl$_3$) δ [ppm]=2.28 (s, 3H, 14-H), 2.29 (s, 3H, 9-H), 2.30 (s, 3H, 10-H), 3.89 (s, 3H, 8-H), 3.90

(s, 3H, 13-H), 3.91 (s, 3H, 11-H), 6.00 (bs, 2H, 7-H, 12-H), 6.69-6.72 (m, 4H, 4-H, 4"-H, 6-H, 6"-H), 6.93 (s, 1H, 3'-H), 7.19 (s, 1H, 6'-H).

$^{13}$C NMR (101 MHz, CDCl$_3$) δ [ppm]=20.33 (C-10), 21.23, 21.26 (C-9, C-14), 56.13, 56.14 (C-11, C-13), 56.17 (C-8), 110.72 (C-4), 111.56 (C-4"), 113.02 (C-3'), 123.69, 123.76 (C-6, C-6"), 124.44 (C-5'), 125.25, 125.53 (C-1, C-1"), 128.88 (C-6'), 129.39 (C-1'), 130.62, 133.66 (C-5, C-5"), 138.05 (C-2'), 140.63, 141.07, 146.40 (C-3, C-3", C-4'), 147.66 (C-2), 155.37 (C-2").

HRMS (ESI, pos. mode): m/z for $C_{24}H_{26}O_5$ (M+Na$^+$): calculated: 417.1678; found: 417.1670

Melting point: 67.7° C. (crystallized from DCM)

The invention claimed is:

1. A process for preparing compounds of the formula (ABA)

by reacting a compound of the formula (A)

with a compound of the formula (B)

with X=—OH or —NR'R";
and R'=H or a protecting group function;
and R"=H or a protecting group function;
or R' and R" may together form covalently bonded protecting group radicals
and $R^1$, $R^2$, $R^3$, $R^4$, $R^6$, and $R^8$ are each independently selected from the group consisting of hydrogen, (C$_1$-C$_{12}$)-alkyl, —O—(C$_1$-C$_{12}$)-alkyl, —N[(C$_1$-C$_{12}$)-alky,]$_2$, —NH(C$_1$-C$_{12}$)-alky, (C$_6$-C$_{20}$)-aryl, O—(C$_6$-C$_{20}$)-aryl, and halogen;
and $R^5$ and $R^7$ are each independently selected from the group consisting of (C$_1$-C$_{12}$)-alkyl, —O—(C$_1$-C$_{12}$)-alkyl, —N[(C$_1$-C$_{12}$)-alkyl]$_2$, —NH(C$_1$-C$_{12}$)alkyl, (C$_6$-C$_{20}$)-aryl, —O—(C$_6$-C$_{20}$)-aryl, and halogen;
where adjacent radicals from the group of the $R^1$ to $R^8$ radicals may be joined via a covalent bond,
characterized in that
the reaction is conducted electrochemically.

2. The process according to claim 1,
characterized in that
the electrochemical process step comprises:
aa) a mixture of at least one solvent and at least one conductive salt is produced,
bb) the compounds to be converted are added to this mixture, with addition of the compound of the formula (A) in a molar excess based on the compound (B),
cc) at least two electrodes are introduced into the reaction solution obtained in bb) and a voltage is applied to the electrodes,
dd) the compounds (A) and (B) are converted to the compound (ABA),
ee) the voltage is switched off and optionally
ff) the compound (ABA) is isolated and/or purified.

3. The process according to claim 1,
characterized in that
the molar ratio of the compound (A) to the compound (B) is in the range from 1.5:1 to 4:1.

4. The process of claim 3, wherein the molar ratio of the compound (A) to the compound (B) is in the range from 1.8:1 to 2.5:1.

5. The process of claim 4, wherein the molar ratio of the compound (A) to the compound (B) is 2:1.

6. The process according to claim 1,
characterized in that
compounds of the formula (A) are compounds in which X=NHR'.

7. The process according to claim 1,
characterized in that
compounds of the formula (A) are compounds in which X=—NH$_2$.

8. The process according to claim 1,
characterized in that
$R^6$ and $R^8$ are identical.

9. The process of claim 8, wherein $R^6$ and $R^8$ are hydrogen.

10. The process according to claim 1,
characterized in that
the reaction is conducted in the presence of a solvent and the solvent is selected from the group consisting of acetonitrile, propylene carbonate, methyl carbonate, nitromethane, ethylene glycol dimethyl ether, methanesulphonic acid, benzene, toluene, water, methanol, ethanol, propanol, isopropanol, halogenated solvents, halogenated or non-halogenated acids, and mixtures thereof.

11. The process according to claim 10,
characterized in that
the solvent is methanol, formic acid, trifluoroacetic acid, hexafluoroisopropanol or mixtures thereof.

12. The process of claim 11, where the solvent is methanol, hexafluoroisopropanol, or mixtures thereof.

13. The process of claim 12, wherein the solvent is hexafluoroisopropanol.

14. The process according to claim 1,
characterized in that
the reaction is conducted without the use of organic oxidizing agents.

15. The process according to claim 1, characterized in that the electrochemical process step is conducted in the presence of at least one conductive salt.

16. The process according to claim 15, characterized in that the counterions of the conductive salts are selected from the group consisting of arsenate, sulphate, hydrogensulphate, alkylsulphate, alkylphosphate, perchlorate, fluoride, aryisulphate, hexafluorophosphate, and tetrafluoroborate.

17. The process according to claim 15, characterized in that the conductive salt is selected from the group consisting of quaternary ammonium borates, ammonium fluoroalkylphosphates, ammonium fluoroalkylarsenates, ammonium trifluoromethylsulphonates, ammonium bis(fluoromethanesulphon)imides, ammonium tris(fluoromethanesulphonyl)methides, methyltributylammonium methylsulphate, methyltriethylammonium methylsulphate, tetrabutylammonium hexafluorophosphate, tetraethylanunonium tetrafluoroborate, lithium hexafluorophosphate, and tetraethylanunonium tetrafluoroborate.

18. The process of claim 17, wherein the conductive salt is methyltriethylammonium methylsulphate or $Bu_3N$ $Me^+MeOSO_3^-$(methyltributylammonium methylsulphate).

19. The process of claim 18, wherein the conductive salt is methyltributylammonium methylsulphate.

20. The process of claim 15, wherein the at least one conductive salt is a tetra($C_1$-$C_6$-alkyl)ammonium or 1,3-di($C_1$-$C_6$-alkyl)imidazolium salt, with the proviso that the alkyl groups may be halogen-substituted.

21. The process of claim 1, wherein protecting group function of R' and R" is selected from the group consisting of tert-butyloxycarbonyl, methyloxycarbonyl, benzyloxycarbonyl, phenyloxycarbonyl, acetyl, trifluoroacetyl, benzoyl, sulphonyl, and sulphenyl.

22. The process of claim 1, wherein R' and R" may together form radicals of the formula PGa or PGb PGa PGb 23. The process of claim 1, wherein $R^1$, $R^2$, $R^3$, $R^4$, $R^6$ and $R^8$ are each independently selected from the group consisting of hydrogen, ($C_1$-$C_{12}$)-alkyl, —O—($C_1$-$C_{12}$)-alkyl, —N[($C_1$-$C_{12}$)-alkyl]$_2$, and halogen.

24. The process of claim 23, wherein $R^1$,$R^2$,$R^3$,$R^4$,$R^6$ and $R^8$ are each independently selected from the group consisting of hydrogen, ($C_1$-$C_{12}$)-alkyl, and —O—($C_1$-$C_{12}$)-alkyl.

25. The process of claim 1, wherein $R^5$ and $R^7$ are each independently selected from the group consisting of ($C_1$-$C_{12}$)-alkyl, —O—($C_1$-$C_{12}$)-alkyl, —N[($C_1$-$C_{12}$)-alkyl]$_2$, and halogen.

26. The process of claim 25, wherein $R^5$ and $R^7$ are each independently selected from the group consisting of ($C_1$-$C_{12}$)-alkyl, —O—($C_1$-$C_{12}$)-alkyl, and —N[($C_1$-$C_{12}$)-alkyl]$_2$.

* * * * *